(12) United States Patent
Parker et al.

(10) Patent No.: US 7,799,266 B2
(45) Date of Patent: Sep. 21, 2010

(54) METHOD FOR MANUFACTURING A STENT DELIVERY SYSTEM

(75) Inventors: Fred T. Parker, Unionville, IN (US); Anthony O. Ragheb, West Lafayette, IN (US)

(73) Assignees: Cook Incorporated, Bloomington, IN (US); MED Institute Inc., West Lafayette, IN (US)

( * ) Notice: Subject to any disclaimer, the term of this patent is extended or adjusted under 35 U.S.C. 154(b) by 0 days.

(21) Appl. No.: 12/336,172

(22) Filed: Dec. 16, 2008

(65) Prior Publication Data
US 2010/0148409 A1 Jun. 17, 2010

Related U.S. Application Data

(62) Division of application No. 11/076,568, filed on Mar. 9, 2005.

(51) Int. Cl.
B29D 23/00 (2006.01)

(52) U.S. Cl. ........................... 264/573; 623/1.23

(58) Field of Classification Search ................ 623/1.23; 264/573
See application file for complete search history.

(56) References Cited

U.S. PATENT DOCUMENTS

| | | | |
|---|---|---|---|
| 5,484,444 A | 1/1996 | Braunschweiler et al. | |
| 5,702,418 A | 12/1997 | Ravenscroft | |
| 5,797,952 A | 8/1998 | Klein | |
| 5,824,041 A | 10/1998 | Lenker et al. | |
| 5,836,965 A * | 11/1998 | Jendersee et al. | 623/1.11 |
| 6,056,906 A | 5/2000 | Werneth et al. | |
| 6,187,013 B1 | 2/2001 | Stoltze et al. | |
| 6,379,365 B1 | 4/2002 | Diaz | |
| 6,607,551 B1 | 8/2003 | Sullivan et al. | |
| 2003/0033001 A1 | 2/2003 | Igaki | |
| 2003/0083646 A1 | 5/2003 | Sirhan et al. | |
| 2003/0208255 A1 * | 11/2003 | O'Shaughnessy et al. | 623/1.11 |
| 2004/0015224 A1 | 1/2004 | Armstrong et al. | |
| 2004/0106977 A1 | 6/2004 | Sullivan et al. | |
| 2004/0249435 A1 | 12/2004 | Andreas et al. | |

OTHER PUBLICATIONS

International Preliminary Report on Patentability for International Application No. PCT/US2006/008423(18 pgs.).
"Zilver® 635 Biliary Stent", Cook Incorporated 2004, (5 pages).
International Search Report for International Application No. PCT/US2006/1008423 (5 pgs.).
The prosecution history of U.S. Appl. No. 11/076,568, shown in the attached Patent Application Retrieval file wrapper document list, printed Mar. 11, 2010.

(Continued)

*Primary Examiner*—Philip C Tucker
*Assistant Examiner*—Alison Hindenlang
(74) *Attorney, Agent, or Firm*—Brinks Hofer Gilson Lione

(57) ABSTRACT

A method for manufacturing a stent delivery system having a holder and at least one stent configured to expand from a first diameter to a second diameter is provided. The manufacturing method includes compressing the stent to the first diameter, inserting the stent into a first tube, placing a second tube inside the first tube and inside an inner diameter of the stent. The second tube is airtight. The manufacturing method also includes applying pressure and heat suitable to the second tube, thereby blowmolding the second tube against the stent.

19 Claims, 7 Drawing Sheets

OTHER PUBLICATIONS

Non-Final Office Action of U.S. Appl. No. 11/076,568, mailed Mar. 19, 2007.
Applicants' Response to Non-Final Office Action, filed Jun. 19, 2007.
Final Office Action of U.S. Appl. No. 11/076,568, mailed Aug. 31, 2007.
Applicants' Response to Final Office Action, filed Oct. 25, 2007.
Non-Final Office Action of U.S. Appl. No. 11/076,568, mailed Feb. 4, 2008.
Applicants' Response to Non-Final Office Action, filed May 7, 2008.
Final Office Action of U.S. Appl. No. 11/076,568, mailed Aug. 18, 2008.
Applicants' Response to Final Office Action, filed Oct. 20, 2008.
Non-Final Office Action of U.S. Appl. No. 11/076,568, mailed Feb. 10, 2009.
Applicants' Response to Non-Final Office Action, filed Jun. 8, 2009.
Final Office Action of U.S. Appl. No. 11/076,568, mailed Aug. 27, 2009.
Request for Pre-Appeal Conference, filed Nov. 24, 2009.
Notice of Panel Decision from Pre-Appeal Brief Review, mailed Feb. 16, 2010.
Appeal Brief, filed Mar. 12, 2010.

* cited by examiner

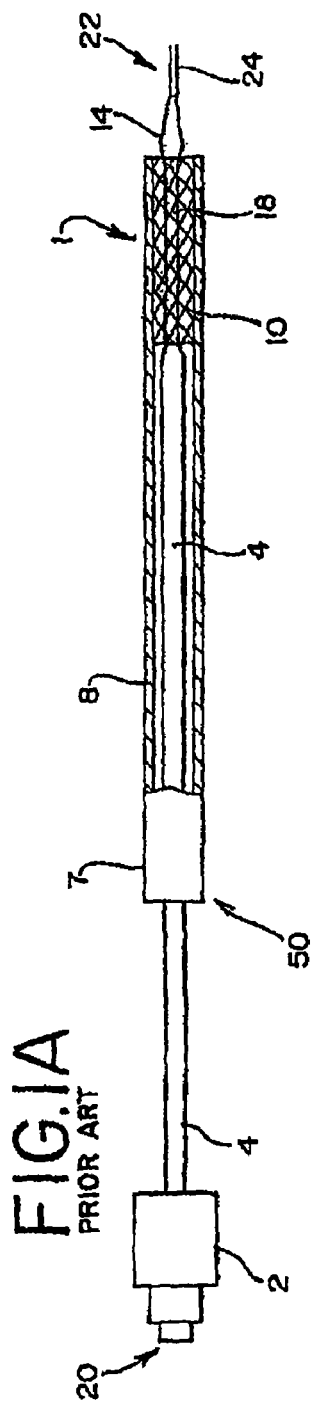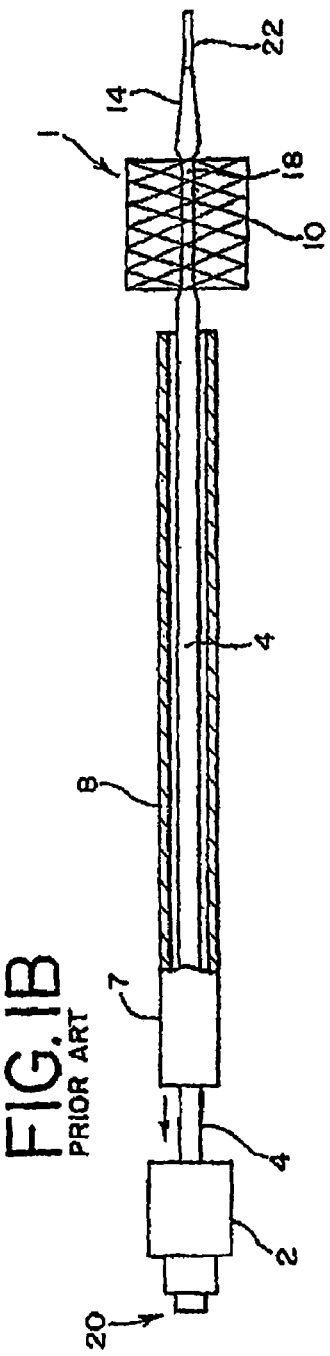

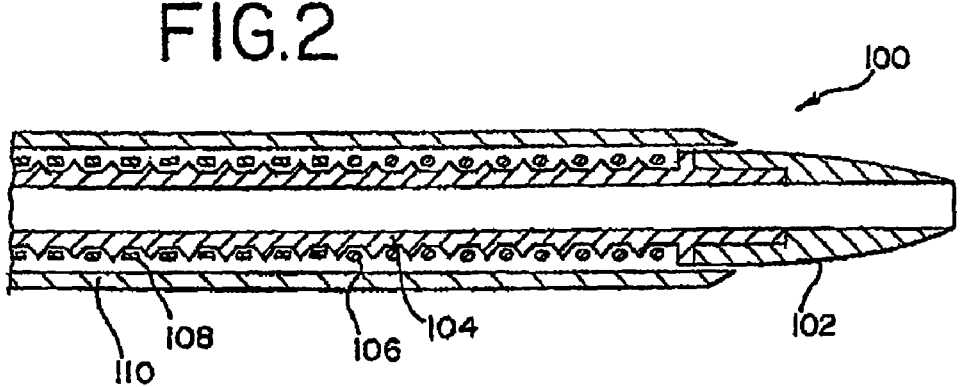
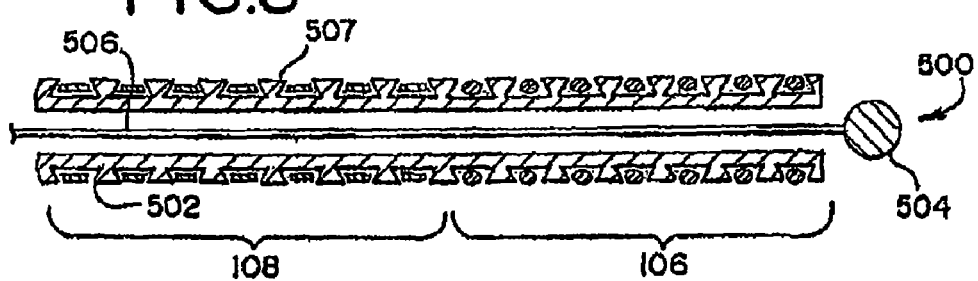

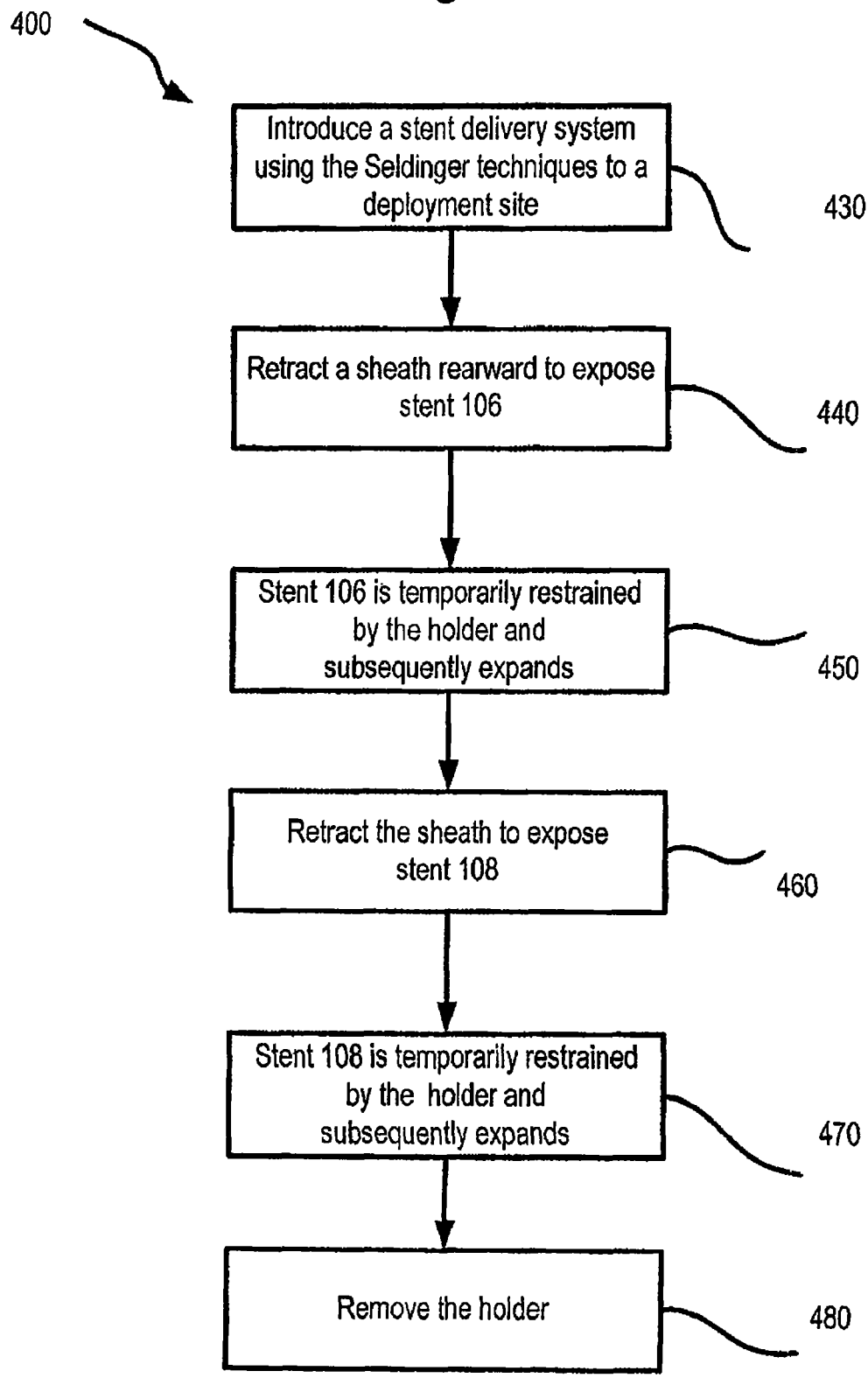

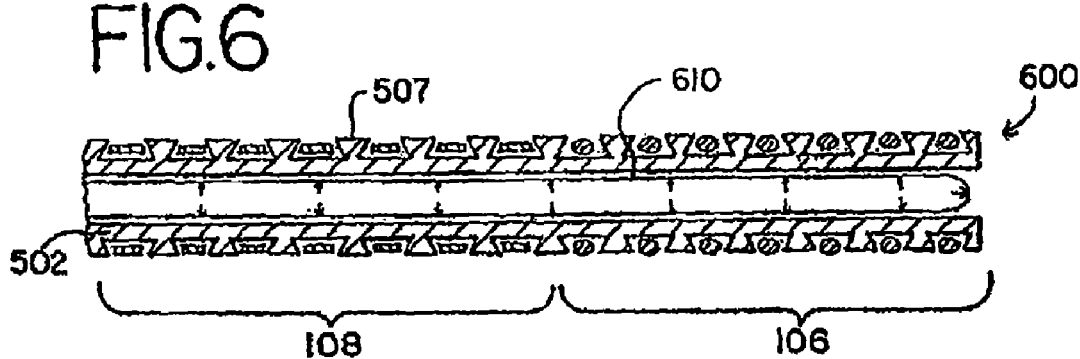
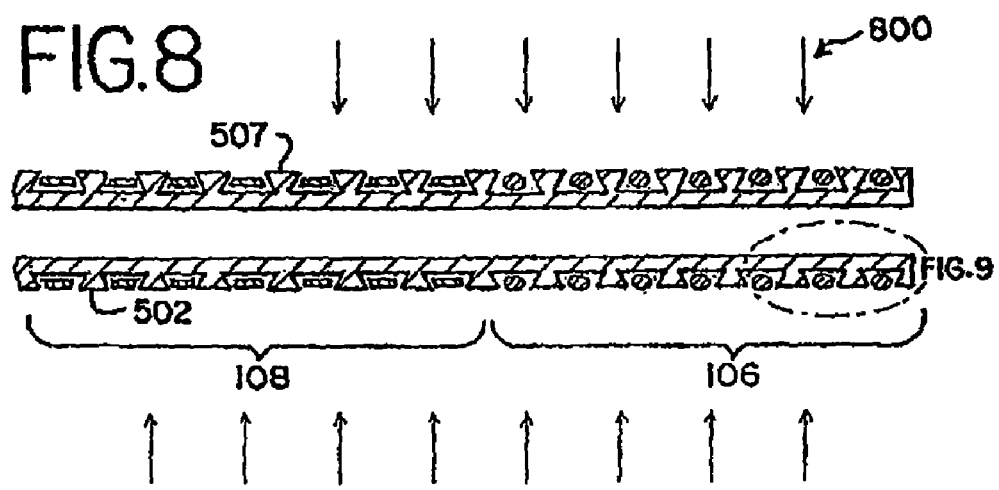
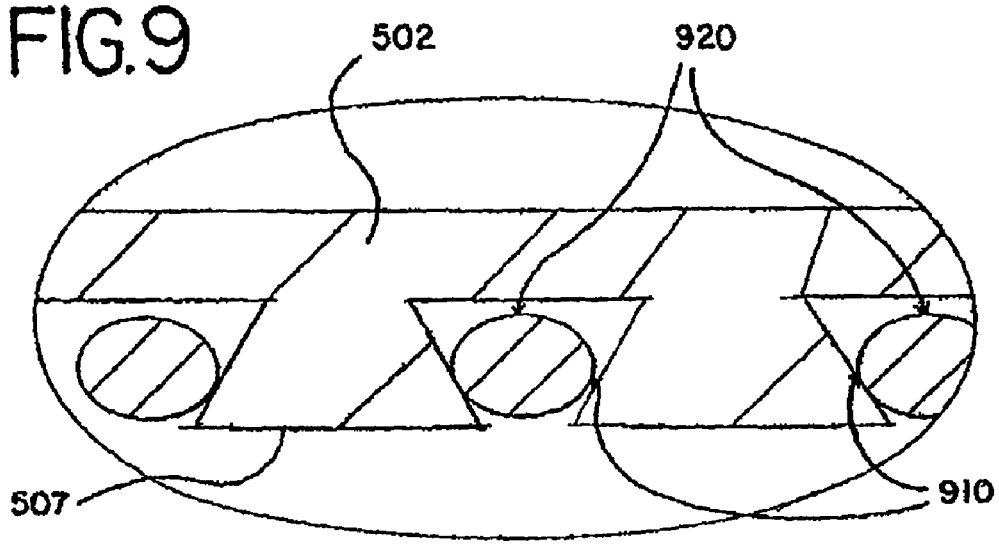

METHOD FOR MANUFACTURING A STENT DELIVERY SYSTEM

PRIORITY CLAIM

This application is a divisional of U.S. application Ser. No. 11/076,568, filed Mar. 9, 2005, the disclosure of which is herein incorporated by reference.

BACKGROUND

1. Technical Field

The invention relates to a method for manufacturing a stent delivery system. More particularly, the invention relates to a method for manufacturing a stent delivery system having a holder interlocking and interfering with a stent.

2. Related Art

Stents are commonly used to treat stenosis of various arteries. Where blood vessels are clogged or narrowed by substances that restrict blood flow, stents are delivered into such vessels and expanded to dilate blood vessels or maintain the dilated state of blood vessels. Expansion of stents may be made with or without the aid of a balloon. Balloon-expandable stents are expanded by inflating a balloon disposed beneath a stent. On the other hand, self-expandable stents are capable of expanding without the use of a balloon. For this purpose, self-expandable stents are generally made from shape memory or spring metal, such as nitinol or stainless steel, so that self-expandable stents are able to expand from a compressed state upon removal of pressures applied thereon.

Determining the proper stent to use is the first step to deploying a stent. The proper stent is determined, in part, based on where a stent is to be deployed. For example, balloon-expandable stents are suitable for coronary arteries, whereas self-expandable stents are more suitable for peripheral arteries. However, the uses of balloon-expandable stents and self-expandable stents often overlap, and each type of stent may be used in a variety of applications. In addition, long lesions or tandem lesions require long coverage. Multiple short stents or a single long stent may be implanted in long lesions or tandem legions.

Once deployed into a human body such as an artery, stents generally remain as permanent implants. Accordingly, stents need to comply with high quality standards and minor manufacturing defects on the stents may result in the manufacturing rejection of the stents. Stents are generally manufactured through complicated and labor-intensive processes. Stent manufacturing processes include laser cutting spring metal to form multiple, interconnected struts of a stent; sandblasting a stent to eliminate debris generated from the laser cutting, and electropolishing processes. Because of these processes, it is more difficult to manufacture long stents with high precision and quality than short stents, in part because a long stent is prone to manufacturing defects along the length compared to a short stent. Where a long stent is rejected due to manufacturing defects, material costs and manufacturing expenses substantially increase.

Although defect-free long stents may be successfully manufactured, conventional stent delivery systems tend to improperly deploy long stents. This is particularly a problem in conventional stent delivery systems where uneven, high forces are applied at the proximal end to push a long stent out of the delivery system upon deployment. FIGS. 1A and 1B illustrate a conventional stent delivery system 1 for a self-expandable stent 10. The stent delivery system 1 includes the self-expandable stent 10, a holder 18 and a sheath 8. The sheath 8 radially constrains the stent 10 during delivery and is retracted when the stent 10 needs to be deployed as shown in FIG. 1B. The holder 18 is disposed beneath the stent 10 and supports the stent 10 during delivery. The stent 10 expands from a compressed state to an expanded state as shown in FIGS. 1A and 1B. The stent delivery system 1 is mounted on one end of a delivery catheter 50. The delivery catheter 50 has an outer tube 8 functioning as a sheath and a core 4, which longitudinally extends from a proximal end 20 to a distal end 22. The core 4 is connected to a hub 2 at the proximal end 20 and to a holder 18 at the distal end 22. The outer tube 8 is connected to a handle 7. A physician deploys the stent 10 by pulling the handle 7 towards the hub 2. As the outer tube 8 is retracted by pulling the handle 7, the stent 10 is exposed and starts expanding. The stent 10 is fully deployed when the handle 7 reaches the hub 2. However, the stent delivery system 1 often experiences problems when the stent to be deployed is long. Deployment of long stents often requires high concentrated force particularly at the proximal end 22 to push the long stent out of the stent delivery system 1. This frequently results in improper or inaccurate deployment of the long stent.

In addition to improper deployment of long stents, the stent delivery system 1 presents other disadvantages as well. One disadvantage is that it is difficult to reduce the size of the stent delivery system 1. It is generally desirable for most stent delivery systems to have a low profile. Stent delivery systems that have lower profiles reduce possible damage to blood vessels during delivery and deployment of the stent. Further, stent delivery systems with lower profiles may be able to get to small and/or tortuous blood vessels. However, the sheath 8 substantially increases the overall profile of the stent delivery system 1. When the sheath 8 is retracted, the stent 10 may unexpectedly and/or uncontrollably move. As previously stated, because the stent 10 is made from spring metal, it tends to expand upon retraction of the sheath 8. This makes it difficult for physicians to accurately position the stent 10. Various attempts have been made to address this problem. For example, structures such as rings and shafts may be added to an inner holder adjacent the proximal end. These structures may engage the proximal end of a stent in order to longitudinally restrain the stent. When the sheath is retracted, the distal end of the stent is first exposed into the blood vessel. Because the proximal end of the stent is temporarily restrained by these structures, the stent may not abruptly move in response to the retraction of the sheath. However, the structures, such as rings and shafts, may be counterproductive to accurate deployment of stents because they trap the stent which must be expanded. In addition, such structures require sophisticated design, which increases manufacturing expenses.

The stent delivery system 1 may not be optimal for delivering and deploying drug coated stents. The stent 10 may include drug coatings on the outer surface thereof. Drugs may be coated on the stent 10 for various purposes. For example, drugs may prevent the formation of scar tissue on the vessel walls or reduce restenosis. Contrary to these benefits, some drug coatings may cause unfavorable consequences if applied improperly. For example, drugs, such as scar prevention drugs, may be highly incompatible with blood. Thus, when drugs that are coated on the stent 10 come into contact with blood, the drugs may cause problems such as blood clots. For this reason, it is desirable that drugs are disposed only on the outer surface of the stent 10. Because the outer surface of the stent 10 is pressed against the vessel walls upon expansion, blood does not flow between the outer surface of the stent 10 and the vessel walls. However, the conventional stents 10 usually contain drug coatings on the sides and inner surfaces which come into contact with the blood. Drug coating material is typically sprayed on a stent 10 when it is in an expanded state. Because the stent 10 is self-expandable, it is generally not possible to spray the drug coating material on the compressed stent 10 since the outer surface of the stent 10 is constantly pressed against the inner surface of a transfer tube or a sheath 8 when it is compressed. When the drug coating material is sprayed on the expanded stent 10, it easily covers the sides and inside surfaces of the stent 10 through the openings between the struts of the stent 10. Further, the stent has relatively large openings when it is expanded. This reduces the efficiency of spraying because a substantial amount of sprayed drugs passes through the openings.

Even if drugs may be adequately sprayed on the expanded stent 10, they may be lost in the course of manufacturing (e.g., loading into the delivery system) and the deployment processes of the stent 10. The stent 10 must be compressed, for example, by rolling it down to a smaller diameter. During this compression process, shear force or mechanical trauma is applied to the stent 10 and a substantial amount of the drug coating may be lost. Further, when the stent 10 is pushed into the sheath 8 and the sheath 8 is later retracted rearward to deploy the stent 10, a substantial portion of the drug coating may be lost. Accordingly, there is a need for a stent delivery system that overcomes the foregoing drawbacks.

SUMMARY

The invention provides a stent delivery system that comprises at least one stent and a holder. The stent is expandable from a compressed state to an expanded state. The holder interlocks and interferes with the stent in the compressed state. An outer diameter of the holder contacts an inner diameter of the stent. For example, the holder may be blowmolded onto an inner surface of the stent in the compressed state. Various other processes are possible to interlock the stent with the holder. The stent delivery system may or may not include sheath. In one embodiment, the sheath may radially constrain the stent. In other embodiment, the sheathless stent delivery system may include a stimulator configured to apply a predetermined force to an inner surface of the holder.

In yet another embodiment, a stent delivery system includes a holder having a pattern or impression. The pattern or impression interlocks and interferes with the stent in the compressed state. The pattern or impression may be formed by a blowmolding process. The pattern or impression does not extend through the stent and contacts side surfaces of the stent. Alternatively, or additionally, the pattern or impression may extend through the stent in the compressed state.

In yet another embodiment, a stent delivery system includes at least one stent having a plurality of radial openings. The radial openings are defined in part by side surfaces of the stent. The stent delivery system further includes a holder having a portion extended from an outer diameter of the holder. The portion of the holder contacts the side surfaces of the stent. Accordingly, the portion restricts longitudinal movement of the stent relative to the holder. When an expansion force of the stent exceeds the restraining force of the holder, the stent is expanded to the expanded state. The stent delivery system further includes a sheath radially constraining the stent. Alternatively, or additionally, the stent delivery system includes no sheath. Instead of the sheath, the portion of the holder further extends around a portion of an outer diameter of the stent. Thus, the portion of the holder may radially constrain the stent. This sheathless stent delivery system further includes means for stimulating an inner surface of the holder, thereby to release the stent from the holder. The stent delivery system further includes a tip attached to the holder at one end of the stent. The holder is made from one of polyethylene terephathalate, crosslink nylon and irradiated polyethelene.

In yet another embodiment, a sheathless stent delivery system includes at least one stent and a holder blowmolded onto an inner surface of the stent in the compressed state. The stent includes a plurality of struts interconnected with one another to form multiple openings therebetween, and the holder includes a plurality of extensions that extend through the multiple openings of the stent. The holder wraps around a portion of an outer surface of the stent, thereby to retain the stent in the compressed state. The sheathless stent delivery system further includes a stimulator adapted to apply a predetermined force to an inner surface of the holder, thereby to release the stent from the holder. For example, the stimulator includes a ball that has a diameter larger than an inner diameter of the holder. The ball is attached to a wire that extends through a hollow interior of the holder. The ball is configured to stimulate the inner surface of the holder as the ball is pulled rearward. The ball is made from a rigid material such as steel. The sheathless system may have an outer diameter smaller than about 0.0540 inch.

In yet another embodiment, a sheathless stent delivery system includes a container positioned inside the holder and storing a liquid supplied thereto. Preferably, the liquid may be compatible with blood. The stent is released from the holder in response to increased pressure of the container. For example, the container may include an occluder.

In yet another embodiment, a stent delivery system includes a holder and a plurality of stents longitudinally arranged one after another. The plurality of stents are expandable from a compressed state and an expanded state. The holder is blowmolded onto an inner surface of stents in the compressed state. The plurality of stents may be different in size, length and/or flexibility. At least one of the plurality of stents may include a drug coating.

In yet another embodiment, the invention provides a method for deploying a stent disposed on a blowmolded holder. The method includes delivering a stimulator attached to a wire to a predetermined deployment site and delivering the compressed stent and the holder to the deployment site by threading the wire through an interior of the holder. The wire may extend from a proximal end to a distal end. The method further includes stimulating an inner surface of the holder by retracting the stimulator toward the proximal end. A diameter of the stimulator is larger than an inner diameter of the holder. The method also includes releasing the stent from the holder, thereby to expand the stent to the expanded state.

In yet another embodiment, a deploying method includes delivering the compressed stent and the holder into a predetermined deployment site and delivering a container into the deployment site and positioning the container inside the holder. The deployment method further includes supplying a quantity of liquid into the container and stimulating an inner surface of the holder in response to an increased pressure of the container. The increased pressure is responsive to supply of the liquid. The method further includes releasing the stent from the holder, thereby to expand the stent to the expanded state.

In yet another embodiment, a deploying method includes (a) delivering the plurality of stents in the compressed state and the holder to a predetermined deployment site and (b) retracting the sheath toward a proximal end to the extent that a first stent is exposed wherein the first stent is disposed distally adjacent a distal end. The method further includes (c) expanding the first stent from the compressed state to the expanded state, (d) retracting the sheath toward the proximal end to the extent that a second stent is exposed wherein the second stent is disposed proximally adjacent the first stent and (e) repeating the step of (a)-(d) until remaining stents are expanded.

In yet another embodiment, a method for manufacturing a stent delivery system is provided. The stent delivery system includes compressing the stent to the first diameter, inserting the stent into a first tube and placing a second tube inside the first tube and inside an inner diameter of the stent. The second tube is airtight. The manufacturing method further includes applying pressure and heat suitable to the second tube, thereby to blowmold the second tube against the stent. The method further includes cooling down the first tube, the stent and the second tube without any pressure. The method also includes inserting the stent and the second tube into a sheath as the first tube is removed, and sealing an end of the second tube during blowmolding and removing the seal after the blowmolding.

The pressure may range between 30 psi and 90 psi. The heat may range between 200° F. and 280° F. Specifically, the pressure may range between 35 psi and 45 psi and the heat ranges between 210° F. and 220° F. More specifically, the pressure is about 40 psi and the heat ranges between 210° F. and 220° F. In other embodiment, the pressure ranges between 85 psi and 95 psi and the heat ranges between 230° F. and 280° F. More specifically, the pressure is about 90 psi and the heat is about 250° F.

In yet another embodiment, a method for manufacturing a sheathless stent delivery system is provided. The method includes compressing the stent from an expanded state to a compressed state, blowmolding the holder against the stent by applying suitable heat and pressure, and applying a drug coating material on an outer surface of the stent in the compressed state. The drug coating material does not cover an inner surface and side surfaces of the stent. The step of applying the drug coating material includes spraying the drug coating material.

The invention provides a stent delivery system having a low profile. The stent delivery system also minimizes damage to blood vessels and properly deploys long stents. The stent delivery system further addresses specific needs of deployment sites, such as blood vessels.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 1A and 1B depict a conventional stent delivery system.

FIG. 2 depicts a first embodiment of a stent delivery system.

FIG. 4 illustrates one embodiment of a method for deploying the stent delivery system of FIG. 2.

FIG. 5 depicts a second embodiment of a stent delivery system.

FIG. 6 depicts a third embodiment of a stent delivery system.

FIG. 8 depicts an exemplary drug coating process.

FIG. 9 depicts an enlarged view of a portion of the stent delivery system of FIG. 8.

DETAILED DESCRIPTION OF THE PREFERRED EMBODIMENTS

Figure 3:
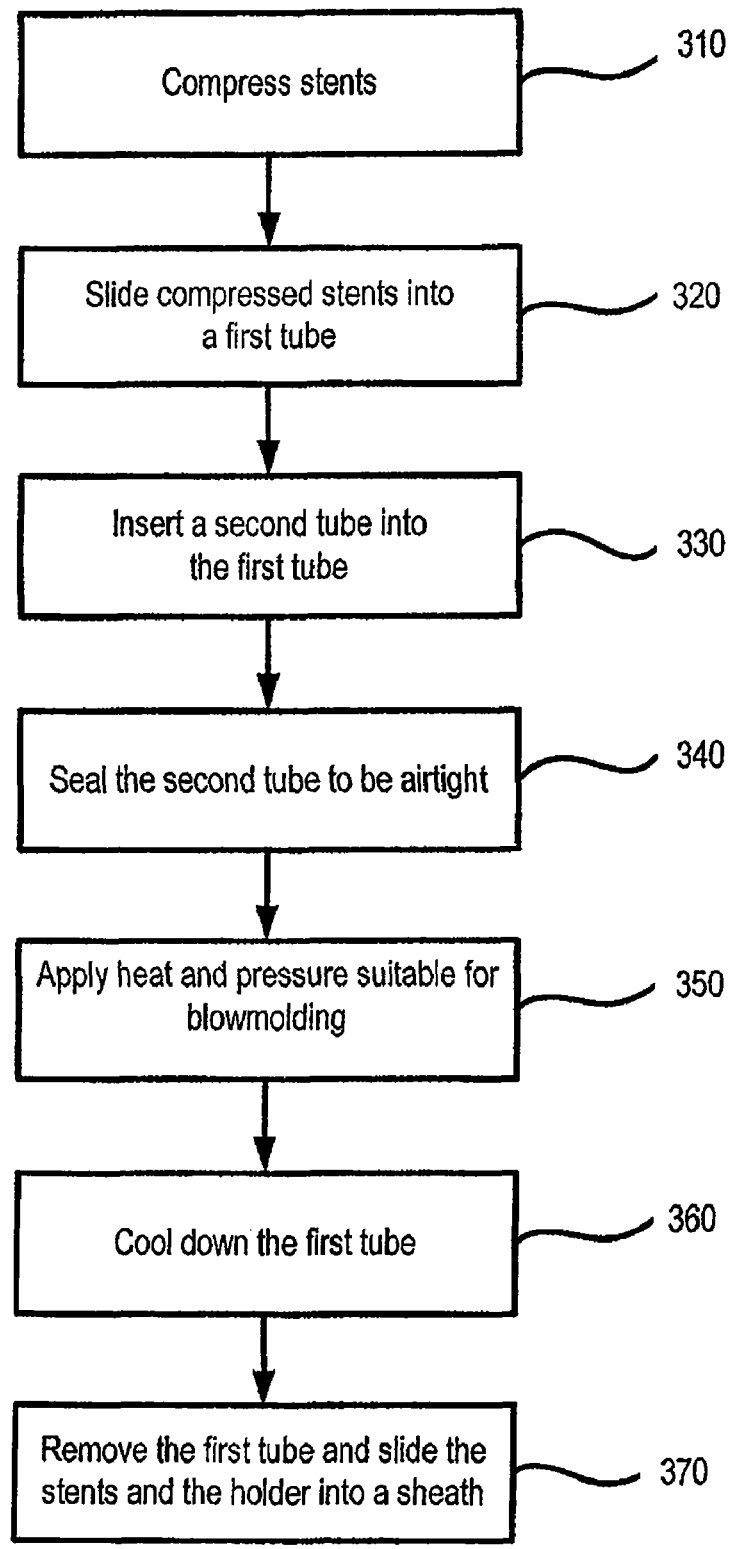
FIG. 3 illustrates one embodiment of a method for manufacturing the stent delivery system of FIG. 2.

FIG. 2 shows a first embodiment of a stent delivery system according to the invention. The stent delivery system 100 includes a first stent 106, a second stent 108, a sheath 110 and a holder 104. At a distal end of the first stent 106, a distal tip 102 is coupled to the holder 104. In FIG. 2, two stents 106 and 108 are delivered by the stent delivery system 100, but delivery of more or less stents is possible. The first stent 106 and the second stent 108 are self-expandable stents, respectively, and expand from a compressed state to an expanded state. The stents 106, 108 have a plurality of radial openings and the radial openings are defined in part by side surfaces of the stents 106, 108. The sheath 110 radially constrains the stents 106, 108 to keep the compressed state. The holder 104 interlocks and interferes with the inner surfaces of the stents 106, 108. Specifically, the holder 104 has a portion extended from its outer diameter and that portion contacts the side surfaces of the stents 106, 108.

For interlocking and interference, the holder 104 has a first pattern or impression as shown in FIG. 2. The stents 106, 108 may be press-fit or friction-fit into the first pattern of the holder. This first pattern or impression of the holder 104 does not extend through the radial openings of the stents 106, 108. Rather, it contacts the side surfaces of the stents 106, 108. To form the first pattern or impression, the holder 104 may be blowmolded. The manufacturing of the holder 104 is not limited to the blowmolding process and various processes are possible. For instance, processes such as casting, injection molding, milling, etching, lithography, electrical discharge machining and laser machining may be used.

When the first pattern or impression of the holder 104 is formed by using the blowmolding process, the holder 104 may precisely conform to inner diameters of the stents 106, 108, as will be described below. A self-expandable stent such as the stents 106, 108 is typically compressed to have a predetermined compressed diameter, regardless of types or sizes of the stents. Although the first stent 106 and the second stent 108 have different diameters upon expansion, they may be compressed to have the same diameter. Accordingly, the holder 104 may support the compressed stents 106, 108, although the stents 106, 108 may be of different types and have different lengths and/or diameters. The tip 102 may be bonded to the holder 104. The distal tip 102 may facilitate navigation of tortuous arteries and vessels during the delivery of the stents 106, 108.

The stent delivery system 100 is manufactured as shown in FIG. 3. The self-expandable stents 106 and 108 are compressed for delivery at block 310. For example, the stents 106 and 108 may be mechanically rolled down to be compressed. Alternatively, or additionally, other known compression methods may be used. Subsequently, the compressed stents 106, 108 are slid into a first tube (block 320). The first tube may be made from any material that has a higher plastically melting threshold than blowmoldable materials. For example, the first tube may be made from steel. The first tube is also made from polytetrafluoroethylene ("PTFE"). PTFE is radially flexible and longitudinally stiff, and therefore, it is frequently used to form a tube that is used for manufacturing stent delivery systems. At the next block 330, a second tube is inserted into the first tube and inside the inner diameters of the stents 106, 108. The second tube may be made from any material that is capable of being blowmolded. For example, polyethylene terephthalate ("PET"), crosslink nylon or irradiated polyethylene may be used to form the second tube. The second tube may have a thick wall and is small enough in diameter to fit inside of the stents 106, 108. The second tube is a pre-form of a final structure, so that it has a substantially similar shape as that of the final structure. By way of example, the second tube may have an outer diameter, 0.050±0.001 inch and an inner diameter, 0.021±0.001 inch. Alternatively, or additionally, the second tube may be thin. The thin second tube may be, in particular, suitable for a stent with a high radial force.

As a process of manufacturing the holder 104, a blowmolding process is described in detail. However, various other processes are available. After the second tube is inserted, it is sealed at the end so that it is airtight (block 340). Next, heat and pressure suitable for blowmolding is applied to the second tube (block 350). For example, heating temperature ranges may be between 200° F. to 240° F. More specifically, the heating temperature may range from 210° F. to 220° F. Air pressure ranges between 35 psi and 45 psi, and more preferably, may be about 40 psi. Under the heat and pressure, the second tube is blown out and is molded to the inner surface of the stents 106, 108. The stents 106, 108 include multiple struts that are made from shape memory or spring metal which are interconnected with one another. A plurality of radial openings are formed between the struts and defined in part by side surfaces of the stents 106, 108. The struts and the radial openings may form the inner surface of the stents 106, 108. The second tube is molded to the struts of the stents 106, 108 and is tightly fitted into the inner diameter of the stents 106, 108. As previously described, the inner diameter of the second tube before the blowmolding may be 0.021±0.001. However, after the blowmolding, the inner diameter of the second tube may be enlarged to have a diameter of about 0.035 to 0.040 inch. The blowmolding process may take a few seconds. For example, it may take about 12 seconds. As a final step (block 360), the first tube, the stents 106, 108 and the second tube are cooled down. While the first tube, the stents 106, 108 and the second tube are exposed to heating and pressure for the blowmolding process, the second tube and the stents 106, 108 push against the first tube. The first tube may be separated from the second tube and the stent by cooling it down. The cooling down process may take a few seconds, for example, 5-10 seconds.

After the cooling down process, the stents 106, 108 and the holder may be released from the first tube. The stents 106, 108 and the holder 104 are then slid into the sheath 110 and at the same time, the first tube is removed by pulling it off the stents 106, 108 (at block 370). The tip 102 may be coupled to the holder 104 at the distal end. Alternatively, or additionally, the tip 102 may be coupled to the holder 104 before the holder 104 is slid into the sheath 110. The stent delivery system 100 is completed and mounted on one end of a delivery catheter for delivery and deployment of the stents 106, 108. The delivery catheter may have the structure similar to the delivery catheter 50 as shown in FIGS. 1A and 1B.

Referring to FIG. 4, delivery and deployment of the stents 106, 108 are described. To deliver the stents 106, 108, the Seldinger techniques may be used at block 430. The Seldinger techniques may involve a needle, a guidewire and a dilator. The stent delivery system 100 is introduced through the dilator and removed therefrom later. When the stent delivery system 100 arrives at the desired deployment site, a physician starts retracting the sheath 110 rearward, i.e., toward the proximal end (block 440). As the sheath 110 is retracted, the first stent 106 becomes exposed and is released. The stent 106 maintains its compressed state until the sheath 110 is sufficiently retracted (block 450). Because the holder 104 is molded to the first stent 106, the holder temporarily restrains a longitudinal movement of the first stent 106. Consequently, abrupt movement of the first stent 106 upon retraction of the sheath 110 is restrained by the holder 104, which allows the physician some time to retract the sheath 110 without being concerned about the abrupt movement of the first stent 106 (block 450). When expansion force of the first stent 106 exceeds the restraining force of the holder 104, the first stent 106 starts to expand. The sheath 110 is then retracted further to expose the second stent 108 at block 460. The second stent 108 is deployed in the same manner as the first stent 106 in block 470. After the stents 106, 108 are fully expanded, the holder 104 is removed from the deployment site at block 480.

Although FIGS. 2-4 illustrate delivery and deployment of the two stents 106 and 108, it is possible to deploy a single long stent or multiple stents with the stent delivery system 100. Where multiple stents are deployed, each stent may have different diameters, special coatings, radial forces and/or flexibility characteristics or combinations thereof. Where an artery is curved or has nonuniform diameters along the length, implanting multiple stents having different diameters and lengths may optimize the treatment of such an artery. For example, if a certain vessel has different diameters along its length, stents corresponding to the different diameters of the vessel may be arranged and deployed in the vessel. Further, if a portion of the vessel needs a certain treatment, a stent to be deployed in that portion may include effective drug coatings. Multiple stents may be arranged to address different needs of various deployment sites. This results in optimized stenting that is specifically tailored to the needs of deployment sites. Furthermore, where a single, long stent is deployed, the holder 104 uniformly restrains the long stent along the longitudinal direction as a result of the blowmolding. Thus, the pressure is evenly distributed along the length of the long stent and does not concentrate on the distal end of the long stent. Accordingly, proper and accurate deployment of the long stents is possible. The stent delivery system 100 also substantially reduces the waste associated with the complicated and costly manufacturing processes of long stents.

FIG. 5 shows a second embodiment of a stent delivery system. Unlike the first embodiment, the stent delivery system 500 is a sheathless stent delivery system. The stent delivery system 500 has no sheath such as the sheath 110. Two stents 106, 108 are delivered by the stent delivery system 500, but more or less stents may be delivered. A holder 502 has a second pattern or impression that extends through the openings of the stents 106, 108, which are formed by multiple struts. The height of the extensions 507 that extend through the openings is adjustable by changing the heat and/or pressure that is applied during the blowmolding process, as will be described in detail below. The second pattern or impression is different from the first pattern or impression shown in FIG. 2 in that the second pattern or impression extends through the opening of the stents 106, 108. The first pattern or impression interlocks or interferes with the stents 106, 108, but it does not extend further. The first pattern may contact side surfaces of the stents 106, 108. To the contrary, the second pattern or impression may partially radially wrap around the stents 106, 108 and press over edges of the stents 106, 108. A tip such as the tip 102 in FIG. 1 may be attached to the holder 502.

The stent delivery system 500 further includes a stimulator such as a ball 504 attached to a wire 506. The wire 506 passes through the center of the stent delivery system 500 as shown in FIG. 5. The ball 504 may be made from any material that is rigid such as steel. The ball 504 may be solid and has a throughhole inside. Alternatively, the ball 504 may be hollow inside. The ball 504 has a diameter that is about the same as the inner diameter of the stents 106, 108 but is not smaller than the inner diameter of the holder 502. In this embodiment, the ball 504 is used as a stimulator, but various other structures are possible. As long as the structure has a diameter that is not smaller than the inner diameter of the holder 502, the shape of such structure is not limited to a ball shape. The ball 504 provides appropriate pressure, stimuli or force to the holder 502. Because the holder 502 extends radially through the stents 106, 108, and more specifically, through the radial openings of the stents 106, 108, it securely restrains the stents 106, 108 from expanding. Accordingly, apart from the nature of the stents 106, 108, i.e., the tendency to expand, a separate force and/or pressure is required to release the stents 106, 108 from the holder 502. As the ball 504 passes through the interior of the holder 502 by pulling back on the wire 506, it continuously stimulates the inner walls of the holder 502.

Alternatively, or additionally, the ball 504 may take the ball 504 in and pushed through the interior of the holder 502. The stent delivery system 500 is already disposed within the blood vessel. The ball 504 attached to the wire 506 may be moved to the blood vessel and pushed through the interior of the holder 502.

The requisite force may differ depending on the flexibility of the holder 502. If the holder 502 is very flexible, a minimum amount of pressure allows the stents 106, 108 to be released from the holder 502. If the holder 502 is more or less rigid, a relatively high pressure may be required. The ball 504 may touch, strike and/or interfere with the inner surface of the holder 502.

The manufacturing process of the stent delivery system 500 is in many ways similar to that of the stent delivery system 100. The stents 106, 108 are compressed and inserted into the first tube made from, for example, PTFE. Then, the second tube which will become the holder 502 is inserted into the first tube and inside the inner diameters of stents 106, 108. The end of the second tube is sealed so that it is airtight, and the second tube is blowmolded to the stents 106, 108 by applying appropriate heat and pressure. As noted above, the holder 502 may be formed with various other processes. Unlike the stent delivery system 100, the stent delivery system 500 typically requires higher pressure and heat than the stent delivery system 100. This is because some portions of the holder 502 are forced to extend through the openings in the stents 106, 108. For example, pressure applied to the stent delivery system during blowmolding ranges from about 85 psi to 95 psi. More preferably, pressure may be about 90 psi. Heating temperature ranges between 230° F. and 280° F., and more preferably, is about 250° F. By adjusting the pressure, temperature or the combination thereof, it is possible to control how far the holder 502 extends radially through the stents 106, 108.

The manufacturing process further allows the stent delivery system 500 to have a compact and tight design. A stent is subject to an electropolishing process that rounds corners off. However, some residual corners may be present even after the electropolishing process. The holder 502 wraps around edges and/or corners of the stents 106, 108, and therefore, the stent delivery system 500 may not interfere with even a small, tortuous blood vessel during the delivery. Further, by radially pressing the stents 106, 108 with the holder 502, the stent delivery system 500 may have a tighter, compact and low profile.

The ball 504 and the wire 506 may be manufactured separately from the stent delivery system 500. The ball 504 is solid and has a main throughhole. The wire 506 may be connected through the main throughhole. The wire 506 may be a guidewire and no additional wire may be required. Alternatively, or additionally, the ball 504 may be hollow and the wire 506 is soldered to the end of the ball 504 as shown in FIG. 3. The ball 504 may be attached to a distal end of a guidewire.

Figure 7A:
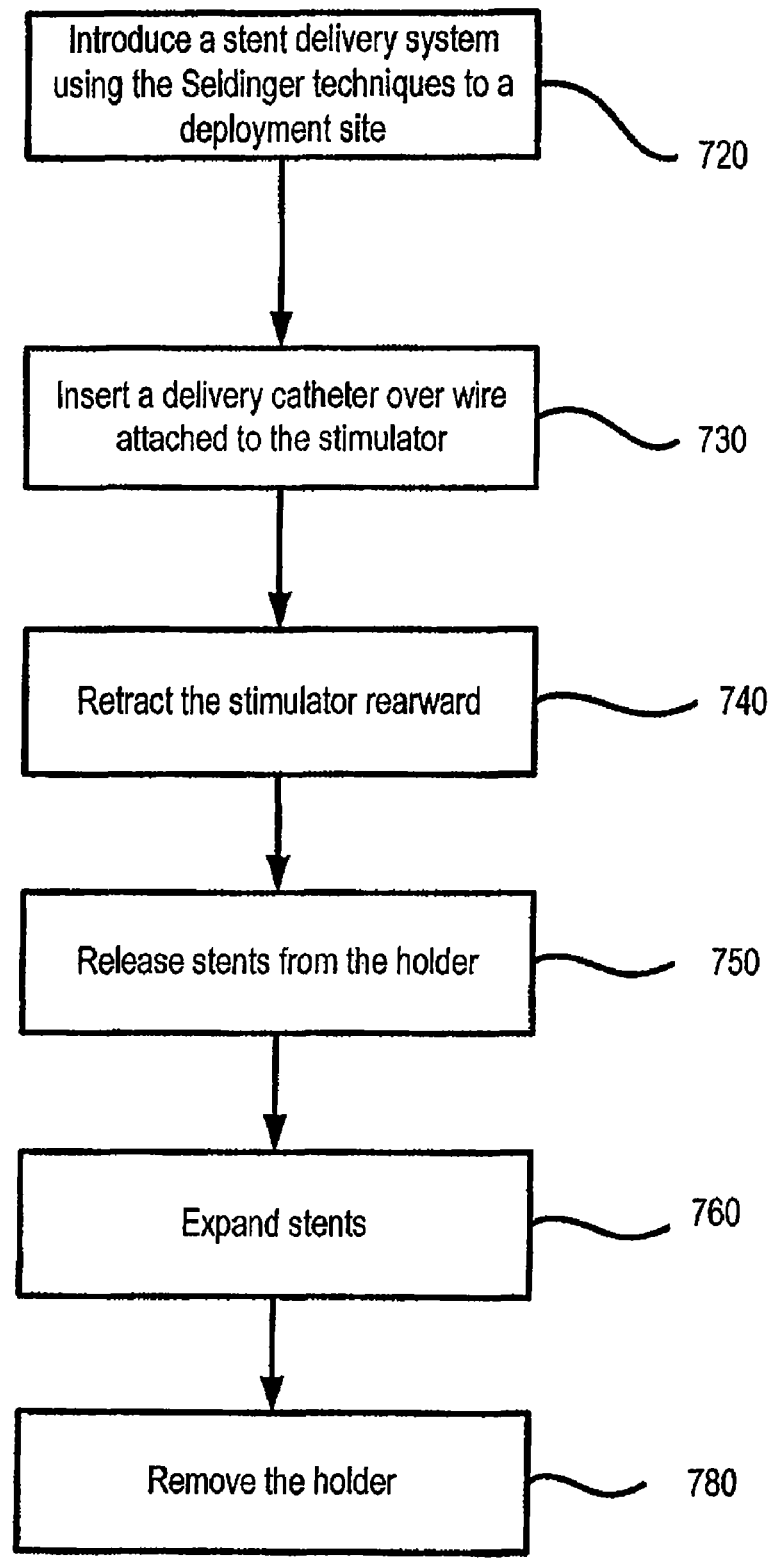
FIG. 7A illustrates one embodiment of a method for deploying the stent delivery system of FIG. 5.

Once the stent delivery system 500 is manufactured, the stents 106, 108 are delivered and deployed. Referring to FIG. 7A, operations of the stent delivery system 500 are described. FIG. 7A illustrates one embodiment of a method for deploying the stents 106, 108 using the stent delivery system 500. The method illustrated in FIG. 7A uses the Seldinger techniques at block 720. The ball 504 and the wire 506 may be used to deploy the stents 106, 108. In this case, the ball 504 bonded to the wire 506 is inserted into a predetermined deployment site, for example, a blood vessel. In this embodiment, a guidewire may not be used. Alternatively, or additionally, it is possible to thread the ball 504 over a guidewire and insert it into the deployment site. In other embodiment, the ball 504 may be taken in and pushed through the blood vessel. Physicians may choose whether the ball 504 is introduced prior to or after the introduction of the stent delivery system 500, depending on their preferences, deployment sites, or many other factors.

The stent delivery system 500 is mounted on one end of a delivery catheter. The delivery catheter is inserted over the wire 506 until the stents 106, 108 arrive at the deployment site (block 730). Because a sheath is not a part of the stent delivery system 500, there is no retraction of a sheath. Instead, the ball 504 is pulled back to apply appropriate force to the holder 502. The ball 504 is retracted rearward by pulling the wire 506 (block 740). Alternatively, or additionally, the ball 506 may be taken in and pushed through. Due to the movement of the ball 504, the inner surface of the holder 502 is stimulated and the stents 106, 108 are released from the holder 506 (block 750). Once released from the holder 502, the stents 106, 108 start to expand at block 760. After the stents 106, 108 are expanded, the holder 502 is removed from the blood vessel, leaving the stents 106, 108 (block 780).

FIG. 6 is a third embodiment of a stent delivery system. A stent delivery system 600 includes the stents 106, 108 and the blowmolded holder 502 having the extensions 507 like the stent delivery system 500. However, instead of the ball 504, the stent delivery system 600 further includes a container device 610. In the stent delivery system 600, a certain type of liquid, which is preferably compatible with blood, may be used to provide pressure to the holder 502. Such liquid may be, for example, saline or carbon dioxide. To supply the liquid, a syringe (not shown) may be connected to a delivery catheter and introduce the liquid into the delivery catheter. Alternatively, handle-turned or knob-turned pressure devices may introduce the liquid into the delivery catheter. The container device 610 may be an artery or vessel occluder. The container device 610 may be required to be disposed inside the holder 502. The container device 610 may block the liquid from flowing into a blood vessel. As the liquid flows into the container device 610, pressure builds up inside the container device as indicated by small arrows in FIG. 6. This built-up pressure provides pressure or stimuli on the inner surface of the holder 502 and makes the holder 502 release the stents 106, 108.

Figure 7B:
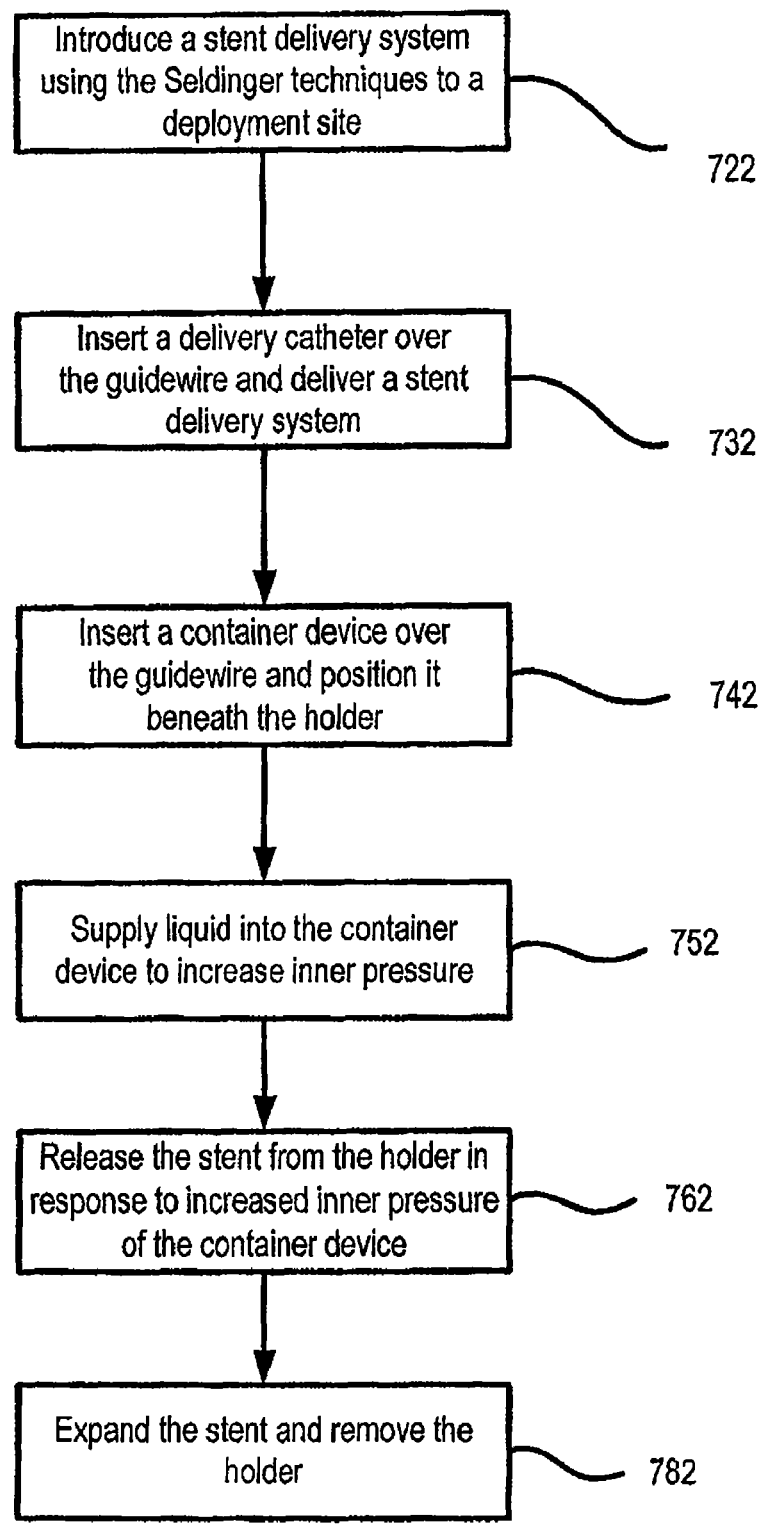
FIG. 7B illustrates another embodiment of the method for deploying the stent delivery system of FIG. 6.

FIG. 7B illustrates another embodiment of a method for deploying stents 106, 108 by using the sheathless stent delivery system 600. In particular, as a stimulator, a certain type of liquid is used to stimulate the inner surface of the holder 502. At block 722, the stent delivery system 600 may be introduced using the Seldinger techniques to a deployment site. The stent delivery system 500 is delivered through a delivery catheter (block 732). After the stent delivery system 500 is delivered to the deployment site, the container device 610 is inserted over the guidewire and positioned inside of the inner surface of the holder 742 at block 742. Alternatively, or additionally, the container device 610 may be inserted before the stent delivery system 500 is delivered. When the container device 610 is placed properly, a certain type of liquid is provided through the delivery catheter to the container device at block 752. Due to the flow of the liquid, the inner pressure of the container device 610 increases and stimulates the inner surface of the holder 502 at block 752. This stimuli, force or pressure by the container device onto the inner surface of the holder 502 makes it possible for the stents 106, 108 to be released from the holder 502 at block 762. As a result, the stents 106, 108 expand and the holder 502 is removed from the deployment site (block 782).

As previously stated, the stent delivery system 500 and 600 do not need a sheath, and therefore, has a lower profile. The stent delivery system 500, 600 have a substantially reduced outer diameter, for example, 0.040~0.060 inches due to absence of a sheath. Specifically, the stent delivery system 500, 600 may have an outer diameter smaller than 0.054 inch. Accordingly, damage to blood vessels which may arise during conventional stenting process may be substantially reduced and manufacturing labor and costs may also be minimized. Furthermore, the stent delivery system 500, 600 provide the same advantages that are provided by the stent delivery system 100.

Another advantage is that the stent delivery system 500, 600 are suitable for delivery and deployment of drug coated stents. FIG. 8 shows one embodiment of a drug coating process for the sheathless stent delivery systems 500, 600. As shown in FIGS. 5 and 6, the sheathless stent delivery systems 500, 600 include the compressed stents 106, 108 and the blowmolded holder 502. The blowmolded holder 502 radially wraps around the stents 106, 108. More specifically, the extensions 507 of the holder 502 securely retain the stents 106, 108. Drug coating material may be applied to the outer surfaces of the compressed stents 106, 108 as shown in FIG. 8. For example, the drug coating material may be sprayed on the compressed stents 106, 108. Alternatively, drug coating materials may be sprayed on the expanded stents 106, 108 if necessary. In other embodiments, only one stent 106 or 108 may be sprayed.

Drug coating materials may include a drug only, a drug mixed with a polymer, or any type of a drug carrier or binder carrying a drug. The drug coating material may have multiple layers including one layer of a drug or one layer of a polymer. The drug carrier or binder may be disposed underneath or on the top of the drug layer. Drugs coated on the stents 106, 108 may include drugs that prevent scar formation, restenosis, etc. These drug coatings may or may not be compatible with blood. For example, drugs for prevention of scar formation may not be compatible with blood. By way of example, drug coating materials may include drugs such as Batimastat, Angiopeptin, ABT 578, Dexamethasone, 17 beta estradiol, Paclitaxel, Myfortic, Endothelial progenitor cells (EPC), surface antibodies, Pimecrolimus, Absorbable MG-alloy, QP-2 Paclitaxel derivative, Everolimus, Sirolimus, Biolimus A7 Biolimus A9, Viral proteins, Actinomycin D, Tranilast, Rapamune, Tacrolimus, C-myc, Cyclosporine, EQs, CD-34 antibody, and/or Tacrolimus. Detailed descriptions on drug coating materials may be found in U.S. Pat. Nos. 5,380,299; 5,609,629; 5,824,049; 5,873,904; 6,096,070; 6,299,604; 6,530,951; 6,730,064; 6,774,278 and U.S. Patent Publication Nos. 2003/28243; 2003/28244; 2003/36794 and 2004/47909, which are incorporated herein by reference.

As shown in FIG. 8, the blowmolded holder 502 tightly wraps around the inside of the stents 106, 108. Specifically, the holder 502 has a portion extended from an outer diameter thereof, i.e., the extensions 507. The extensions contact the side surfaces of the stents 106, 108 such as side surfaces 910 shown in FIG. 9 and restrict longitudinal movement of the stents 106, 108 relative to the holder 502. Further, the extensions 507 of the holder 502 extend around a portion of an outer diameter of the stents 106, 108 and radially constrain the stents 106, 108. As a result, no sheath is required for delivery and deployment of the stents 106, 108. Without a sheath, the stents 106, 108 remain compressed and are able to be deployed. Sprayed drug coatings may be applied only on the outer surface of the stents 106, 108. Because the outer surfaces of the stents 106, 108 are pressed against vessel walls, blood does not flow between the outer surfaces of the stents 106, 108 and the vessel walls. FIG. 9 depicts an enlarged view of a portion of the stent delivery system 500, 600. The stents 106, 108 include the side surfaces 910 disposed at its radial openings. The radial openings are defined in part by the side surfaces. The stents 106, 108 also have inner surfaces 920. The drug coating material may be precisely sprayed on the outer surfaces of the stents 106, 108 and does not spread to the sides 910 and/or inside surfaces 920 of the stents 106, 108. Unlike the outer surface, the sides 910 and/or inside surfaces 920, 930 of the stents 106, 108 may contact blood. Therefore, even if the drug coatings are incompatible with blood, no restenosis, blood clots or related problems occur because the drugs do not reside on the sides 910 and/or the inside surfaces 920, 930 of the stents 106, 108. Further, because the drug coatings may be sprayed on the compressed stents 106, 108, loss of the drug coatings through large openings of the expanded stents 106, 108 and compression processes of the stents 106,108 may be substantially minimized. In addition, the drug coatings are not lost due to a sheath since the stent delivery system 500 is sheathless.

The advantages of the effective drug coatings may be achieved regardless the holder 502. The holder 502 may be made from materials that have high or low surface tensions. Upon application of the drug coatings, the holder 502 with high surface tension may keep drug coatings thereon and loss of the drug coatings may be minimized. Alternatively, the holder 502 with low surface tension may not keep the drug coatings thereon. Instead, the drug coatings may flow onto the stents 106, 108 interfered with the holder 502. Loss of the drug coatings may be again reduced.

Although various embodiments have been described in connection with a stent delivery system, the invention is not limited to the described embodiment of the stent delivery system. The invention may be applicable to other medical systems or methods that involve implantation of a device or structure like a stent. The application of the invention may be more useful if the device or structure has characteristics of self-expansion.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. A method for manufacturing a stent delivery system having a holder and at least one stent configured to expand from a first diameter to a second diameter, wherein the second diameter is larger than the first diameter, comprising:

compressing the stent to the first diameter, wherein the stent is self-expandable without requiring a balloon;

inserting the stent into a first tube;

placing a second tube inside the first tube and inside an inner diameter of the stent, wherein the second tube is airtight;

applying pressure and heat suitable to the second tube, and blowmolding the second tube against an inner surface of the stent to convert the second tube into the holder having a cylindrical body and a plurality of edges wrapping around at least a portion of the stent such that the stent is expanded to the second diameter by flexing the plurality of edges without substantially expanding the cylindrical body of the holder; and separating the first tube from the stent and the blowmolded second tube after cooling down the stent and the blowmolded second tube.

2. The method of claim 1, wherein the pressure ranges between 30 psi and 90 psi.

3. The method of claim 1, wherein the heat ranges between 200° F. and 280° F.

4. The method of claim 1, wherein the pressure is about 40 psi and the heat ranges between 210° F. and 220° F.

5. The method of claim 1, wherein the pressure is about 90 psi and the heat is about 250° F.

6. The method of claim 1, further comprising cooling down the first tube, the stent and the second tube without any pressure.

7. The method of claim 1, further comprising inserting the stent and the second tube into a sheath as the first tube is removed.

8. The method of claim 1, further comprising sealing an end of the second tube during blowmolding and removing the seal after the blowmolding.

9. The method of claim 1, further comprising:

applying a drug coating material on an outer surface of the stent in the compressed state after the second tube is blowmolded against the stent.

10. The method of claim 9, wherein the step of applying the drug coating material includes spraying the drug coating material.

11. The method of claim 9, wherein the drug coating material does not cover an inner surface and side surfaces of the stent.

12. The method of claim 1, wherein the second tube is made from one of polyethylene terephathalate, crosslink nylon and irradiated polyethelene.

13. The method of claim 1, wherein the first tube is made from polytetrafluoroethylene.

14. The method of claim 1, further comprising forming a pattern or impression of the holder configured to be customized to be a shape of the stent in a compressed state.

15. The method of claim 14, wherein forming the pattern or impression comprises forming the plurality of edges configured to radially and longitudinally restrict a strut of the stent in the compressed state and to touch a portion of a radially outwardly exposed side surface of the strut of the stent, wherein the plurality of edges is integrally formed with the holder.

16. The method of claim 14, wherein applying pressure and heat further comprises:

applying pressure and heat suitable to the second tube during blowmolding of the second tube wherein an outer diameter at the pattern or impression of the holder is adjustable based on the pressure and the heat.

17. The method of claim 16, wherein the outer diameter at the pattern or impression of the holder is approximately the same as an outer diameter of a strut of the stent in the compressed state.

18. The method of claim 16, wherein the outer diameter at the pattern or impression of the holder is restricted to an inner diameter of the first tube.

19. The method of claim 1, wherein the second tube comprises a polymer tube blowmolded to the inner surface of the stent by using the stent as a mold for blowmolding.

* * * * *